United States Patent [19]

Dede et al.

[11] Patent Number: 4,863,897

[45] Date of Patent: Sep. 5, 1989

[54] PROTEIN AND MINERAL WATER-CONTAINING COSMETIC COMPOSITIONS

[75] Inventors: László Dede; Mária Dede née Pál; László Bogdány; Olga Bogdány née Forgács, all of Budapest, Hungary

[73] Assignee: Caola Kozmetikai és Háztartásvegyipari Vállalat, Budapest, Hungary

[21] Appl. No.: 81,603

[22] Filed: Aug. 3, 1987

Related U.S. Application Data

[63] Continuation of Ser. No. 705,336, filed as PCT HU84/00036 on Jun. 1, 1984, published as WO84/04885 on Dec. 20, 1984, abandoned.

[30] Foreign Application Priority Data

Jun. 3, 1983 [HU] Hungary .............................. 1991-83

[51] Int. Cl.$^4$ ...................... A61K 37/02; A61K 7/00; A61K 33/00
[52] U.S. Cl. ........................................ 514/6; 514/802; 530/380; 530/829; 530/830; 424/101; 424/195.1; 424/617; 424/618; 424/630; 424/639; 424/641; 424/646; 424/649
[58] Field of Search .................... 424/101, 195.1, 127; 530/380, 829–831; 514/6, 802

[56] References Cited

U.S. PATENT DOCUMENTS 4,177,261 12/1979 Dietze et al. ..................... 424/101

FOREIGN PATENT DOCUMENTS 506381 5/1976 U.S.S.R. .............................. 424/101

OTHER PUBLICATIONS

U.S. Dispensatory, "Mineral Waters", pp. 1277–1278.

Primary Examiner—Johnnie R. Brown
Assistant Examiner—Jacqueline M. Stone
Attorney, Agent, or Firm—Schweitzer & Cornman

[57] ABSTRACT

This invention relates to cosmetic, health- and body-preserving compositions of high biological value, optimizing the biological processes occurring in the skin cells and providing the most preferable function of the enzyme system of the cells connected with the age of the organism.

The compositions of the invention contain in addition to the commonly used carrier and additive and/or filling materials and active ingredients, mineral waters of a native condition, medicinal waters and/or the mixtures thereof and/or the mixtures thereof with fermented or non-fermented plant juices and/or optionally inorganic materials playing the role of trace elements in the living organism as well as proteins.

10 Claims, No Drawings

PROTEIN AND MINERAL WATER-CONTAINING COSMETIC COMPOSITIONS

This is a continuation of co-pending application Ser. No. 705,336 filed as PCT HU84/00036 on Jun. 1, 1984, published as WO84/04855 on Dec. 20, 1984, now abandoned.

This invention relates to a cosmetic composition of high biological value, optimizing the biological processes occurring in the skin cells and providing the most preferable function of the enzyme system of the cells connected with the age of the organism.

The aim of the invention is to provide the restoration and preservation of the cells and the skin by using natural substances. According to the invention, this aim is accomplished by treating proteins, suitably prepared from the blood or from the elements thereof with inorganic materials occurring as trace elements in the organism, or with natural, river-, lake-, sea-, mineral and medicinal waters, with inorganic materials obtained from these waters.

It is known that the trace elements participating of the active transfer and being components of a number of various enzymes, exert a decisive influence on the function of the living organism. Their deficiency, e.g. that of copper, iron or zinc leads to the degeneration of the cellular activity; thus the cell respiration, the hematopoiesis, brain tissues, lungs and nervous system also become damaged. Although the primary role of a cosmetic appearing for a superficial viewer is the care of the skin, it can be stated that the harmonized function and health of the living organism and that of its parts should not be considered as a result of distinct effects, since all organs and tissues or the organism are in mutual interaction.

The disorders arising from the deficiency of trace elements exert a general influence on the organism and hence also on the condition of the skin which is most striking for the observer. The skin is a highly differentiated organ and its condition has a decisive influence on the aesthetic appearance of a man.

In many cases the elimination of the disorders arising from the deficiency of the trace elements is not a simple task since the absorption of the salts of trace elements, e.g. of iron sulfate in a form capable of taking a sufficient part of the physiological processes is not satisfactory per se.

From among the trace elements, the role of which is known, zinc, copper, iron, cobalt, manganese, silicium and magnesium, etc. are essential for the skin. Thus, 20 percent of the zinc content of the human organism are found in the skin. Zinc plays an important role in the protein synthesis of the skin. Copper has a high importance in the structural development of the collagen and elastin, in addition to its well known effect on the blood count. When these trace elements are not present in a sufficient amount, the solubility of the collagen and elastin is increased and their function is deficient. Manganese and magnesium take part in a number of enzyme reactions, e.g. of the collagen synthesis, however their effects on the activity of the enzymes regulating the nucleic acid metabolism are also significant. Silicium plays an important role in the structural development of both the collagenous and cartilaginous tissues. In addition to the trace elements mentioned above, a number of other ones, such as selenium as well as sulphur, sulphides, vanadium and nickel also possess important roles. Practically all inorganic materials are significant for the optimum function of a living cell, which is not surprising while considering that all these materials were present in the primary ocean, at the appearance of the life.

There are cosmetics containing trace elements as well as other cosmetic compositions utilizing various proteins known for providing distinct types of activities, e.g. moisturizing ability, etc. These agents, however, do not mean an optimum solution for the supply of the skin and that of the organism through the skin with trace element biocatalysts since the trace elements cannot be absorbed advantageously from an aqueous medium either per se or in their common organic complexes. Thus skin or rheumatic disorders react with conflicting and widely scattering results to medicinal baths and mineral water therapy or are even ineffective, though the balneologists might expect an unambiguous, preferable action of these baths and mineral waters on the basis of the quality and quantity of the inorganic salts of these waters. It is known that the compositions of medicinal and mineral waters used for decades or centuries show nearly no or a few differences; that of the sea-water can be considered as stable under natural conditions. In spite of these facts the utility of these waters is varying or they are even inactive for patients suffering from frequently identical skin disorders or diseases. As the composition of mineral waters containing mostly the trace elements needed to the skin and organism, is stable, the reasons for these extreme results should be found in the individual characteristics of the patients. Likely, the reason for the divergent results consists in that the carrier molecules transferring the trace elements are not always available. The trace elements, inorganic salts and ions as such cannot freely diffuse through the skin into the living organism and the cells to a sufficient extent and cannot be bound to the enzymes; this occurs only by the aid of the carrier molecules. These carriers can specifically transfer only a single, defined trace element to the site of the action and it can be supposed that these carriers are present in the blood.

Thus, the aim of this invention is to use the plasma proteins as a whole by treating those with trace elements, mineral, medicinal, natural waters and with the materials thereof to obtain compositions possessing a satisfactory skin beneficiating cosmetic activity.

It was found that compositions can be obtained which show an extraordinarily outstanding activity for the care of skin, by treating the proteins, e.g. prepared from the blood or blood elements with the appropriate trace elements and optionally by heating the mixture obtained.

By treating the blood elements, e.g. plasma proteins with microelements, mineral and medicinal waters, with inorganic materials obtained therefrom, as well as with natural plant juices and extracts, cosmetics with an excellent and surprising effect may be prepared, such as that described e.g. in Example 6.

The cosmetics prepared according to the invention are highly useful for the cosmetic care and restoration of the skin.

The beneficial effect of the compositions of the invention is intensified when in addition to or instead of medicinal waters, the mixtures of plant extracts and/or plant juices with medicinal waters, the mixtures of natural waters and/or extracts and the solutions thereof enriched with the required trace elements are used as aqueous phases of the compositions of the invention.

The compositions and embodiments of the invention are illustrated by the following non-limiting Examples.

EXAMPLE 1

A mixture containing 137.5 g of white petrolatum/-vaseline/, 82.5 g of cetyl alcohol, 27.5 g of paraffin oil and 27.5 g of Tween 60 is heated to 80° C. to form the fatty phase of the composition. Meanwhile, 10 g of plasma protein prepared from cattle blood plasma are swollen in 200 ml of the medicinal water of Harkány and the mixture is heat-treated at 112° C. for 90 minutes. After the treatment with the medicinal water, the protein is cooled to 60° C. and mixed to the fatty phase kept at 80° C. After homogenation, a further amount of 600 ml of the medicinal water of Harkány heated to 70° C. are added to the hot mixture and the whole are stirred until cool. A cream is obtained which possesses an excellent moisturizing, cosmetic skin-restoring effect.

EXAMPLE 2

The process described in Example 1 is followed, except that 1 mg of gold /III/-trichloride is added to the plasma protein before or after the heat treatment.

EXAMPLE 3

The process described in Example 1 or 2 is followed, except that the medicinal water of Hajduszoboszló is used as an aqueous phase.

EXAMPLE 4

The process described in Example 1 or 2 is followed, except that the medicinal water of Parád is used as an aqueous phase.

EXAMPLE 5

The process described in Examples 1 to 4 is followed, except that the plasma protein is treated with a medicinal water, 200 ml of which contain 1 mg of gold/III/-trichloride, 0.5 mg of silver nitrate, 0.1 mg of chromic chloride, 2 mg of ferrous sulphate, 1 mg of manganous chloride, 1 mg of ammonium molybdate, 0.5 mg of cupric sulphate, 1 mg zinc chloride, 0.5 mg cobaltic chloride, 0.2 mg of boric acid and 0.2 mg of nickelous sulphate added before the heat treatment.

EXAMPLE 6

The process described in Example 1 is followed, except that the plasma protein is treated with 200 ml of the medicinal water arising from the Lukács-bath /Budapest/ which contain 1 mg of ferrous sulphate, 1 mg of cupric sulphate, 0.5 mg of nickelous sulphate, 1 mg of zinc sulphate and 0.5 mg of cobaltic chloride added previously.

EXAMPLE 7

The process described in Examples 1 to 6 is followed, except that the geyser water of Karlsbad is used as the aqueous phase of the composition.

EXAMPLE 8

The process described in Examples 1 to 7 is followed, except that the natural water of Balaton is used as an aqueous phase.

EXAMPLE 9

The process described in Example 1 is followed, except that the plasma protein is heat-treated with 200 ml of distilled water and then 600 ml of sea-water, e.g. of the water of the Aegean Sea is used for preparing the cream.

EXAMPLE 10

The process described in Examples 1 to 6 is followed, except that in addition to 200 ml of medicinal water employed to treat the plasma protein, the natural water of the Danube river is used for preparing the cream.

EXAMPLE 11

The process described in Example 1 is followed, except that the plasma protein is treated with the medicinal water in the presence of 2 mg of zinc sulphate.

EXAMPLE 12

The process described in Example 1 is followed, except that, instead of the medicinal water a water is used which contains in 1 ml each 5 $\mu$g of copper, 5 $\mu$g of iron, 10 $\mu$g of zinc, 2 $\mu$g of cobalt, 1 $\mu$g of nickel, 20 $\mu$g of magnesium and 20 $\mu$g of calcium.

EXAMPLE 13

The process described in Example 1 is followed, except that carrot juice is used as an aqueous phase.

EXAMPLE 14

The process described in Examples 1 to 6 is followed, except that a wine prepared from grape is used as an aqueous phase.

EXAMPLE 15

The process described in Examples 1 to 6 is followed, except that apple vine neutralized by sodium hydrogen carbonate is used as an aqueous phase.

EXAMPLE 16

The process described in Examples 1 to 6 is followed, except that a fruit juice, e.g. apple juice is used as an aqueous phase.

EXAMPLE 17

80 ml of water and 2 g of sodium hydrogen carbonate are added to 20 ml of swine blood, then the mixture is kept at 120° C. for 1 hour. The material obtained is filtered and 700 ml of the medicinal water of Harkány are added to the filtrate. The aqueous solution obtained is worked up to a cream in a manner known in the art to give an excellent, moisturizing and cosmetic skin-restoring (skin-preserving) cosmetic.

EXAMPLE 18

2 g of sodium hydrogen carbonate, 50 ml of aqueous camomile extract and 600 ml of the medicinal water of Héviz are added to 100 ml of sheep blood plasma. The mixture is stirred at 20° C. for 1 hour, then it is worked up to a cosmetic body-preserving cream in a manner known in the art.

EXAMPLE 19

The process described in Example 1 is followed, except that, instead of the medicinal water of Harkány, an 1:1:1 mixture containing the medicinal waters of Harkány, Hajduszoboszló and Héviz is used as an aqueous phase.

EXAMPLE 20

The plasma protein prepared from 10 g of swine blood is treated with 200 ml of the medicinal water of Héviz at 120° C. for 1 hour. To the solution obtained, 300 ml of the natural medicinal water of Héviz are added, the mixture is filled to ampoules of 2 ml volume and sterilized after sealing. This ampouled composition is suitable for the cosmetic preservation of the skin by manual infriction or by iontophoresis.

EXAMPLE 21

2 mg of ferrous sulphate, 1 mg of manganous chloride, 1 mg of cupric sulphate, 1 mg of zinc sulphate and the extract prepared from 1 g of camomile with 20 ml of hot water are added to 100 ml of native cattle blood plasma. The mixture is heated to 80° C. under intensive stirring to give a jelly-like material with a highly moisturizing and cosmetic skin-restoring-preserving effect.

EXAMPLE 22

The process described in Example 20 or 21 is followed, except that instead of the medicinal water of Héviz, an 1:1 mixture containing the medicinal water of Harkány and Hajduszoboszló is used.

EXAMPLE 23

To a plasma protein powder prepared from 10 g of cattle blood, 200 ml of the medicinal water of Harkány kept at 70° C. are added and the mixture is heated at 112° C. for 90 minutes. After cooling, 70 ml of natural medicinal water of Harkány, 30 g of Alfozide KT-25, 80 g of Zala betaine, 570 g of sodium lauryl ether sulphate, 20 g of Alfid-D-11, 2 g of Alphasept (a preservative), 10 g of polyethyleneglycol M-200 and 10 ml of 96% ethanol are added to the mixture to give an excellent cosmetically refreshing, skin-restoring cosmetic foam bath.

EXAMPLE 24

A plasma protein prepared from 10 g of swine-blood is treated with 200 ml of the medicinal water of Harkány at 120° C. for 1 hour, then 125 ml of the medicinal water of Harkány and 125 ml of the medicinal water of the Lukács-bath /Budapest/ are added to the solution obtained. This mixture is supplemented with an appropriate preservative and used in spray form to treat the skin injuries caused by sunburn.

EXAMPLE 25

A plasma protein prepared from 10 g of rabbit blood is treated with 200 ml of the medicinal water of Hajduszoboszló at 112° C. for 90 minutes, then 300 ml of the medicinal water of Balf and 50 ml of sea-water are added to the hot solution. Then 92 g of Alfozide KT-25, 75 g of Zala betaine, 190 g of sodium lauryl ether sulphate, 10 g of Alfid-D-11 and 2 g of Alphasept are added to the mixture to give an outstanding hair shampoo.

EXAMPLE 26

A plasma protein powder prepared from 10 g of cattle blood is swollen with 200 ml of the medicinal water of Harkány while stirring and kept at 112° C. for 1 hour. To the solution obtained, 300 ml of a medicinal water of Harkány are added which contain 0.2 mg of ferrous sulphate, 0.2 mg of zinc sulphate, 0.2 mg of cupric sulphate, 0.1 mg of nickelous sulphate and 0.1 mg of cobaltic chloride. The mixture obtained is filled to ampoules of 2 ml volume and sterilized by heat. This composition excellently inhibits sebum deposition on sebum formation on the scalp.

EXAMPLE 27

A plasma protein prepared from 10 g of swine blood is transformed to a solution by treating with 100 ml of the medicinal water of Hajduszoboszló and 100 ml of the medicinal water of Harkány at 120° C. To this solution, a melt containing 100 g of cetyl alcohol, 101 g of isopropyl myristate, 220 g of sorbitol of 70%, 60 g of cosmetic stearin, 140 g of cosmetic vaseline oil, 2 g of glutaraldehyde, 39.2 g of cosmetic lanolin, 20 g of propyleneglycol and 3 g of Nipagin M is added. The mixture is supplemented with 1100 ml of medicinal water of Hajduszoboszló kept at 60° C. and with 5 g of potassium hydroxide and stirred until cool. This composition is excellently useful as a hand-preserving balsam to restore the skin disorders caused by e.g. detergents.

EXAMPLE 28

800 g of a soap powder is dissolved in 2 liters of distilled water at 80° C., thereafter 200 g of sodium lauryl ether sulphate, a plasma protein solution prepared from a cattle blood of 5% with 200 ml of medicinal water of Harkány at 120° C., as well as 500 ml of glycerol, 8 g of Nipagin and an odour are added and stirred until cool. An excellent cream soap is obtained which inhibits the damaging of the skin and is particularly suitable to keep the inflammated skin in a clean state.

EXAMPLE 29

142 g of stearin is saponified by 28.5 g of potassium hydroxide in 500 ml of distilled water at 80° C., then a solution prepared from 10 g of plasma protein with 200 ml of the medicinal water of Héviz at 160° C., as well as 100 g of sodium lauryl ether sulphate, 100 g of glycerol, 3 g of Nipagin M preservative agent are added and stirred until cool. An outstanding cleaning agent is obtained which inhibits the damaging and drying of the skin.

EXAMPLE 30

To a melt prepared from 25 g of cetyl alcohol, 12 g of vaseline, 2.5 g of Tween 60 and 5 g of glycerol at 72° C., a plasma protein solution of 1% prepared with 6 ml of the medicinal water of Héviz at 120° C. as well as 5 ml of ethanol are added. The mixture is coloured and aromatized as desired to give a lip-preserving agent which diminishes the desiccation of the lips.

EXAMPLE 31

A mixture containing 137.5 g of white petrolatum /vaseline/, 82.5 g of cetyl alcohol, 27.5 of paraffin oil and 27.5 g Tween 60 is heated to 80° C., 700 ml of a medicinal water of Harkány kept at 60° C. are added and the mixture is stirred until cool to give an excellent hydratating cream which is useful for the preservation of the inflamed skin.

EXAMPLE 32

The process described in Example 31 is followed, except that a mixture containing 350 ml of the medicinal water of Harkány and the extract of 3 g of camomile prepared with 350 ml of hot water is used as an aqueous phase.

EXAMPLE 33

The process described in Example 31 or 32 is followed, except that 1 mg of ferrous sulphate, 1 mg of zinc sulphate, 1 mg of cupric sulphate, 0.5 mg of nickelous sulphate, 0.5 mg of manganous sulphate and 0.2 mg of ammonium molybdate are dissolved in the aqueous phase before mixing.

EXAMPLE 34

A salt mixture obtained by evaporating 0.5 g of the medicinal water of Harkány is mixed with 200 ml of distilled water, the plasma protein prepared from 10 g of cattle blood plasma is added and the mixture obtained is heat-treated at 121° C. for 2 hours. The material obtained is worked up to a cream according to the Example 1.

What we claimed is:

1. A cosmetic composition comprising from about 0.1% to about 5% by weight of a protein from blood or from blood plasma, said protein having been treated with a mineral water.

2. The composition of claim 1, wherein the mineral water contains from about 0.00001% to about 0.0009% by weight based on the composition, of a trace element.

3. A composition as claimed in claim 1, wherein the mineral water is water selected from group consisting of mineral water from the Hungarian Lukacs bath in Budapest and mineral water from the Hungarian Harkany.

4. A composition as claimed in claim 1, wherein the mineral water includes one or more of the following additionally dissolved trace elements Au, Ag, Pt, Cr, Fe, Mn, Co, Cu, Ni, Zn, Mg and Ca.

5. A composition as claimed in claim 2, wherein the trace elements are selected from the group consisting of Au, Ag, Pt, Cr, Fe, Mn, Co, Cu, Ni, Zn, Mg and Ca.

6. A process for preparing a cosmetic composition, comprising treating a protein from blood or from blood plasma with a mineral water, and heating the mixture, and then formulating the composition by adding from about 0.1% to about 5% of the treated protein thereto.

7. The process of claim 6, wherein the mineral water contains from about 0.00001% to about 0.0009% by weight based on the composition of a trace element.

8. A process as claimed in claim 7, wherein the trace elements are selected from the group consisting of Au, Ag, Pt, Cr, Fe, Mn, Co, Cu, Ni, Zn, Mg and Ca.

9. A process as claimed in claim 6, wherein the said protein is in the form of blood plasma selected from the group consisting of cattle blood plasma and pig blood plasma, which plasma is mixed with the said mineral water.

10. A process as claimed in claim 6, wherein the mineral water is selected from the group consisting of water from the Hungarian Lukacs bath in Budapest and water from the Hungarian Harkany bath.

* * * * *